United States Patent [19]

Koshiishi

[11] 4,222,670
[45] Sep. 16, 1980

[54] LIQUID SAMPLE ANALYZER

[75] Inventor: Kiyozo Koshiishi, Sagamihara, Japan

[73] Assignee: Olympus Optical Co., Ltd., Tokyo, Japan

[21] Appl. No.: 921,336

[22] Filed: Jul. 3, 1978

[30] Foreign Application Priority Data

Jul. 26, 1977 [JP] Japan ............................. 52-89449

[51] Int. Cl.³ ................. G01N 21/25; G01N 1/10; G01N 27/26
[52] U.S. Cl. .......................... 356/414; 356/246; 356/440; 204/195 M
[58] Field of Search ............ 356/246, 409, 414, 440; 250/576; 204/195 M

[56] References Cited

U.S. PATENT DOCUMENTS

| 2,048,128 | 7/1936 | Logan | 356/246 |
| 3,236,602 | 2/1966 | Isreeli | 23/253 |
| 3,997,420 | 12/1976 | Buzza | 204/195 M X |
| 3,999,861 | 12/1976 | Bellinger | 356/246 |
| 4,135,999 | 1/1979 | Schindler et al. | 204/195 M X |

OTHER PUBLICATIONS

"Direct Potentiometric Measurement of Potassium in Blood Serum with Liquid Ion–Exchange Electrode", Wise et al., Clinical Chemistry, vol. 16, #2, 1970, pp. 103–106.

*Primary Examiner*—Vincent P. McGraw
*Attorney, Agent, or Firm*—Ostrolenk, Faber, Gerb & Soffen

[57] ABSTRACT

A liquid sample analyzer comprises an open, sample determining channel in the form of a small gap, means for supplying liquid sample to the channel, means for injecting a fluid into the channel to rinse its interior, and means for determining the optical density or the ion concentration of the liquid sample supplied to the channel. In this manner, the concentration of liquid sample such as blood is automatically determined and analyzed.

8 Claims, 4 Drawing Figures

LIQUID SAMPLE ANALYZER

BACKGROUND OF THE INVENTION

The invention relates to a liquid sample analyzer, and more particularly, to such apparatus which analyzes a liquid sample through light absorbance or ion electrode process.

The concentration of liquid sample, such as blood, is automatically determined and analyzed by using a light absorbance analyzer or ion electrode analyzer. A conventional arrangement of light absorbance analyzer is illustrated in FIG. 1. Referring to FIG. 1, light from a light source 1 is split in two directions, one being passed through an optical filter 2a to produce monochromatic light, which is transmitted through a collimator lens 3a into a colorimetric cell 8b. Light passing through the cell 8b impinges on a light receiving element 4a, which converts the light output into an electrical signal, which is in turn supplied to one input terminal 5a of an operational amplifier 5 as a sample signal. The remaining portion of the light from the source 1 is passed through another optical filter 2b to produce monochromatic light, which is then passed through a collimator lens 3b to impinge on another light receiving element 4b as a reference light. In response to the light input, the element 4b produces an electrical reference signal, which is supplied to the other input terminal 5b of the amplifier 5. The amplifier 5 effects a comparison of the sample signal and the reference signal, and the analyzer output is recorded by a recorder 6.

The cell 8b is formed as part of a colorimeter tube 8 which comprises a transparent piping. The colorimeter tube 8 is centrally formed with a U-bend 8a, the right-hand limb of which is shaped as a T-section which includes a sample supply portion 8c and an air bubble remover 8d, and the left-hand limb of which communicates with the colorimetric cell 8b which extends horizontally and which is in turn in communication with a vertically extending liquid drain 8e. A sample is contained within the cell 8b and the collimated light from the lens 3a is passed therethrough. Sample 7, such as blood, which is supplied to the colorimetric tube 8 is fed through the supply portion 8c while it is partitioned by air bubbles 9. However, immediately before the sample 7 enters the U-bend 8a, it is automatically debubbled by the remover 8d which has an open top. Subsequently, the sample 7 flows into the cell 8b where its concentration is determined with transmitting light, and is finally disposed of through the drain 8e.

A major problem with the arrangement described above is a contamination of the cell 8b, which results in a degradation in the accuracy of analysis. Such contamination may be prevented by flushing an old sample off the wall of the cell with an increased flow of new sample 7. Alternatively, an aqueous standard solution may be passed through the cell between the measurement of successive samples, thus flushing away an old sample which remains attached to the wall of the cell. However, such techniques disadvantageously require the use of a waste solution in large quantities. In addition, as will be noted from FIG. 1, the closed construction of the colorimetric cell 8b makes it difficult to remove any bubble 9 which might have made its way into the cell 8b, resulting in noises which appear in the result of determination.

FIG. 2 shows an exemplary arrangement of conventional analyzer which utilizes the ion electrode technique. As shown, an ion concentration detector comprises a glass tube 11 through which a quantity of liquid sample 12 is supplied, an ion electrode 13 which is connected in communication with the glass tube 11 by means of connecting tube 14 and including a sample passage tube 15, a support tube 21 which is connected in communication with the tube 15 by means of connecting tube 20, and a double junction reference electrode 19 mounted on the support tube 21 and having its lower end disposed in contact with sample 12 contained within the tube 21. In the example shown, the ion electrode 13 is formed as a glass electrode for detecting Na ions, and comprises sample passage tube 15 formed of Na ion-sensitive glass film such as Li-Al-Si, An-Al-Si or similar composition, AgCl electrode 16 coiled around the tube 15, an outer tube 17 which contains the electrode 16 and the tube 15, and a filling of internal standard solution 18 contained in the tube 17.

The reference electrode 19 comprises an outer tube 23, a porous member 22 secured to its lower end for contact with liquid sample 12 and having a port 23a formed in its sidewall for replenishing a reference solution 27, an inner tube 25 disposed within the outer tube 23 and having a porous member 24 secured in its lower end for contact with the reference solution 27 contained within the outer tube 23 and having a port 25a formed in its sidewall and extending through the outer tube for replenishing reference solution, AgCl electrode 26 disposed within the inner tube 25, a quantity of external reference solution 27 which fills the outer tube 23, a quantity of internal reference solution 28 which fills the inner tube 25, and a cap 29 to which the tubes 23, 25 and electrode 26 are secured together. The electrode 26 is in electrical contact with liquid sample 12 through reference solution 28, porous member 24, reference solution 27 and porous member 22.

The ion electrode 13 and reference electrode 19 are connected to input terminals 30a, 30b, respectively, of an amplifier 30, the output terminal 30c of which is connected with an indicator 31. The Na ion concentration in the liquid sample 12 is determined as a potential difference across the ion electrode 13 and the reference electrode 19 which is proportional to the logarithm of Na ion concentration. The potential difference is amplified by the amplifier 30 and is displayed by the indicator 31.

In the arrangement of FIG. 2, a contamination of sample passage tube 15 and porous member 22 again poses a problem, causing a degradation in the accuracy of analysis. The prior art practice to avoid this has been to flush away an old sample with an increased quantity of sample 12, again resulting in a wasteful use of sample solution, in particular when the liquid sample is blood.

SUMMARY OF THE INVENTION

It is an object of the invention to provide a liquid sample analyzer which avoids the disadvantages of the prior art by providing a liquid sample determining cell in the form of a channel formed as a small gap and which is open laterally, and by providing a rinsing unit which injects a fluid toward the channel.

In accordance with the invention, a colorimetric cell or ion concentration detector which represents the liquid sample determining cell is formed as a laterally open channel which may be defined by a small gap. This minimizes the quantity of liquid sample required for the measurement. The open construction of the channel, combined with the pressure of the liquid sample which is maintained higher than the atmospheric pressure, allows any air bubble which remains in the sample to be removed out of the channel, thus completely eliminating the generation of noises which may be caused by bubbles. The channel is rinsed by the injection of a fluid such as air, and the high rinsing effect completely eliminates the likelihood of the channel being contaminated, thus allowing a high accuracy of analysis.

DESCRIPTION OF PREFERRED EMBODIMENTS

Figure 3:
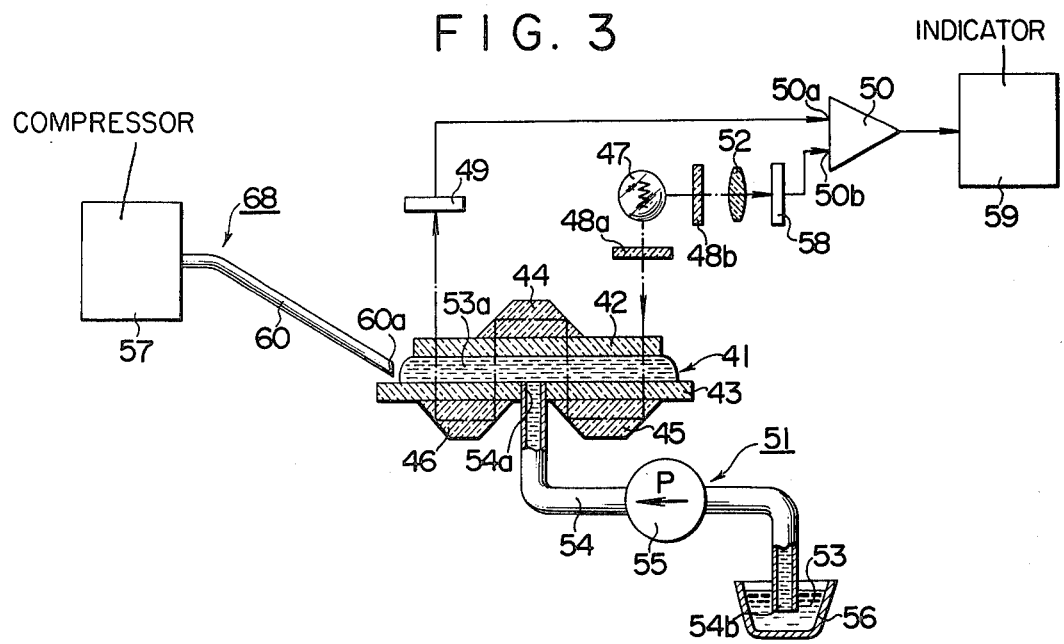
FIG. 3 is a schematic view, partly in section, of the light absorbance analyzer according to one embodiment of the invention.

Referring to FIG. 3, there is shown a liquid sample analyzer according to the light absorbance technique which is constructed in accordance with one embodiment of the invention. A sample determining channel 41 is shown in enlarged cross section. The channel 41 is defined by a pair of transparent plates 42, 43 which are disposed opposite to each other with a small gap or clearance therebetween. The channel is laterally open, and defines a colorimetric cell. The upper plate 42 is centrally provided with prism 44 which is secured to the outside thereof for conducting light therethrough. Similarly, the lower plate 43 has a pair of prisms 45, 46 secured to the outside thereof which also define a light path. These prisms serve to guide light from a light source 47 so as to transmit through liquid sample 53a supplied into the channel 41 a plurality of times and to direct the transmitting light to a photometric, light receiving element 49.

Light from the source 47 is split in two directions. In one direction, the light is passed through an optical filter 48a to be converted into monochromatic light before it impinges on the channel 41. Successive refractions of the light by the prisms 45, 44, 46 permit it to transmit through the liquid sample 53a a plurality of times and to cause it to impinge on the element 49 subsequently. The element 49 responds to the impinging light input by providing an electrical signal indicative of the absorbance of the sample, which signal is applied to one input terminal 50a of an operational amplifier 50. Light split in the other direction is passed through an optical filter 48b to be converted into monochromatic light, and thereafter passed through collimator lens 52 to impinge on a light receiving element 58 as reference light. The element 58 responds to the reference light by providing an electrical signal, which is applied to the other input terminal 50b of the amplifier 50 as a reference signal. The amplifier 50 effects a comparison of the reference signal and the absorbance signal, and its output is displayed on an indicator 59 which is calibrated in terms of concentration.

Liquid sample 53 is supplied to the channel 41 through a conduit 54 by means of a sample supply unit 51 which includes a pump 55 and a sample cup 56. One end 54a of the conduit 54 extends centrally through the lower plate 43 and opens into the channel 41 while its other end 54b opens into the cup 56 which contains a quantity of liquid sample 53. It will be noted that pump 55 is connected in the conduit 54. Thus the pump withdraws liquid sample 53 from the cup 56 and delivers it through conduit 54 into the channel 41 as sample 53a. Since the channel 41 is formed as a small gap, the capillary action contributes to supplying the sample 53 into the channel.

A rinsing unit 68 comprising a compressor 57 and a nozzle 60 connected therewith is disposed adjacent to the channel 41. The nozzle 60 has its free end 60a disposed in proximity to the channel 41 so that fluid such as air, distilled water, buffer solution or the like may be injected therefrom to rinse the interior of the channel 41, namely, the volume defined between the plates 42, 43. The compressor 57 initiates its operation simultaneously with the pump 55, which however continues to operate for a given time interval after the compressor 57 is deenergized. This interval is sufficient to fill the channel 41 with liquid sample 53a.

In operation, the pump 55 is initially operated to deliver liquid sample from the cup 56 into the channel 41. At the same time, the compressor 57 is operated to inject air, for example, from the nozzle 60, so that the channel 41 is cleaned by the supply of both air and liquid sample. When it is completely rinsed, the compressor 57 is deactuated. However, the pump 55 continues to operate for a given time interval until the channel 41 is filled with sample 53a to be determined, whereupon the pump is also deactuated. The quantity of liquid sample 53 required for this process is small. Since channel 41 is formed as a small gap which is open laterally, any bubble contained in the sample 53 is driven out of the channel 41 inasmush as the liquid pressure of the sample 53 is higher than the atmospheric pressure. In this manner, noises which may be caused by the presence of bubbles are avoided.

When the liquid sample 53a is supplied to the channel 41, light from the source 47 is caused to transmit through the sample a plurality of times for the purpose of the photometric determination. An analytical result of a high accuracy is assured since contamination of the channel 41 is avoided and noises caused by the presence of bubbles are prevented. The result is displayed on the indicator 59 in terms of concentration after it is amplified by the amplifier 50.

In the embodiment described above, the conduit 54 extends through the plate 43. However, the end 54a of the conduit 54 may be disposed laterally of the channel 41 so that the sample is supplied from a lateral side of the channel.

Figure 4:
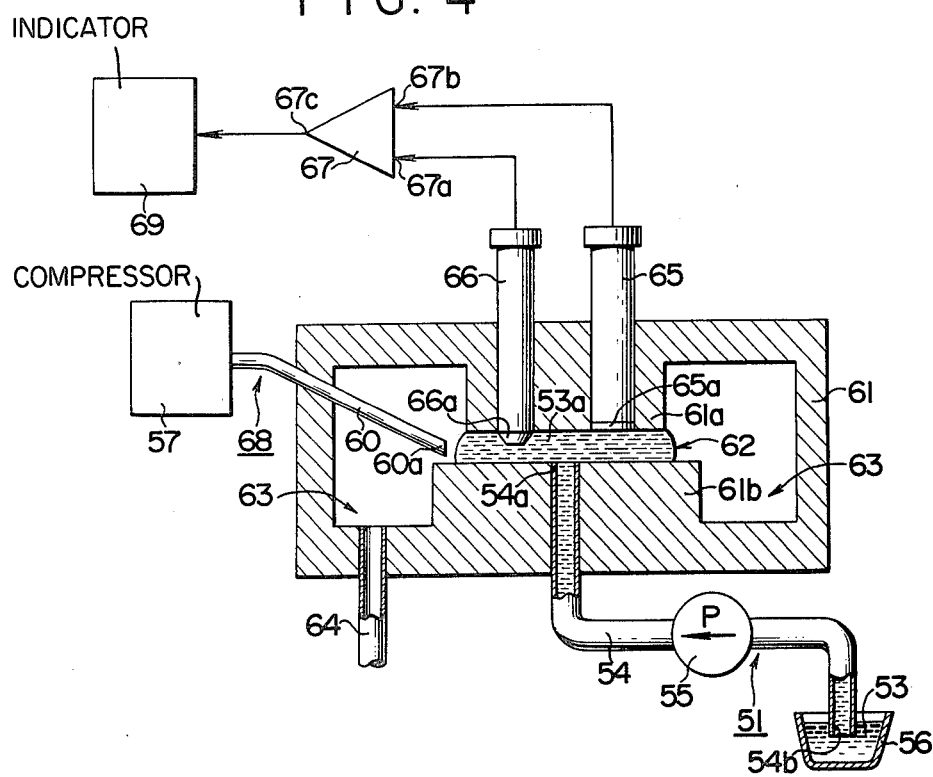
FIG. 4 is a schematic view, partly in section, of the ion electrode analyzer according to another embodiment of the invention.

FIG. 4 shows another embodiment of the invention which represents a liquid sample analyzer according to the ion electrode technique. The sample supply unit 51 and the rinsing unit 68 are constructed in the same manner as shown in FIG. 3, and therefore corresponding parts are designated by like numerals without repeating their description.

The ion concentration is detected in a box-shaped electrode cell 61, which is centrally provided with a sample determining channel 62 defined by a pair of projections 61a, 61b which are separated by a small clearance. The projections 61a, 61b may be designed in any desired configuration since liquid sample 53a supplied into the channel 62 is maintained therein by the surface tension.

Figure 1:
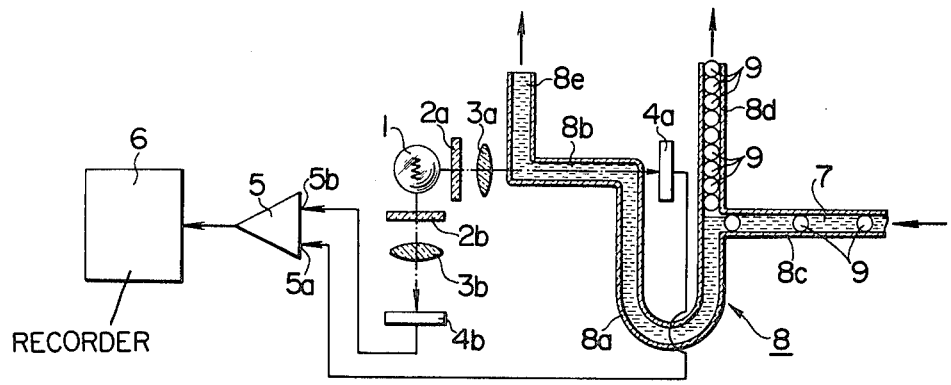
FIG. 1 is a schematic view, partly in section, of a conventional liquid sample analyzer according to the light absorbance technique.
Figure 2:
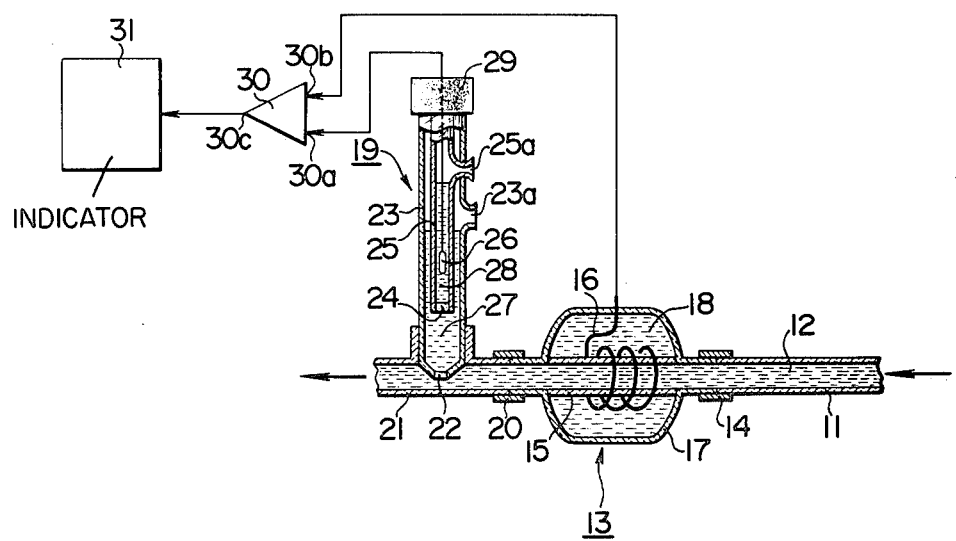
FIG. 2 is a similar view showing the arrangement of a conventional liquid sample analyzer which is constructed according to the ion electrode technique.

An open chamber 63 laterally surrounds the channel 62 and is connected with a drain pipe 64 which communicates with the exterior so that the liquid sample can be discharged out of the cell 61 after the rinsing step and the determination step. A conduit 54 extends centrally through the lower projection 61b and has its one end 54a opening into the channel 62. An ion detecting electrode 65 and a reference electrode 66 are mounted in the upper projection 61a so that their ends 65a, 66b are in contact with liquid sample 53a supplied to the channel 62. These electrodes 65, 66 are basically identical to the electrodes 13, 19, respectively, which have been described in connection with FIG. 2 for determining Na ion concentration of the sample 53a in the form of a potential difference. These electrodes 65, 66 are connected with input terminals 67a, 67b of an amplifier 67, the output terminal 67c of which is connected with an indicator 69.

In operation, when the pump 55 is driven, the rinsing step and the supply of liquid sample 53 to the channel 62 take place in the same manner as in the arrangement of FIG. 3. Consequently, such operation will not be described. The present embodiment operates by detecting the concentration of Na ions contained in the liquid sample 53a which has been supplied to the channel 62 as a potential difference across the ion detecting electrode 65 and the reference electrode 66, and the potential difference is amplified by the amplifier 67 to be displayed on the indicator 69 in terms of ion concentration. Again, the invention achieves a high rinsing effect, which prevents contamination of the channel, thus allowing an analytical determination of high accuracy.

What is claimed is:

1. A liquid sample analyzer comprising: a sample determining channel formed as a small gap which is laterally open about a sufficient portion of its perimeter that any bubble in a liquid sample contained in said channel is expelled from said channel when the fluid pressure of said liquid sample is greater than atmospheric pressure; a sample supply unit for supplying said liquid sample into said channel; a rinsing unit for injecting a fluid into said channel to rinse the interior of said channel; and means for determining the optical density or ion concentration of said liquid sample located in said channel.

2. A liquid sample analyzer according to claim 1 in which said means for determining the optical density comprises a colorimetric cell formed by a pair of transparent plates disposed in opposing relationship with a small clearance therebetween to provide said channel, a plurality of light conducting prisms disposed on the outside of said plates for causing light from a photometric light source to transverse said liquid sample a plurality of times and for conducting it to a light receiving element.

3. A liquid sample analyzer according to claim 2 in which the light from said light source is converted into monochromatic light by means of an optical filter before it is introduced into said liquid sample.

4. A liquid sample analyzer according to claim 1 in which said means for determining the ion concentration comprises an electrode cell which is centrally provided with opposite projections separated by a small clearance to provide said channel, and an ion detecting electrode and a reference electrode mounted in said cell so that their end is disposed in contact with said liquid sample supplied to said channel.

5. A liquid sample analyzer according to claim 4 in which said electrode cell is box-shaped, and wherein an open chamber laterally surrounds said channel and is connected with a drain pipe.

6. A liquid sample analyzer according to claim 1 in which said sample supply unit comprises a sample cup for containing a quantity of liquid sample, a sample feed pump for withdrawing liquid sample from said cup, and a conduit for conducting the liquid sample to said channel.

7. A liquid sample analyzer according to claim 1 in which said rinsing unit comprises a nozzle having one end free and located adjacent to said channel, and a compressor cooperating with said nozzle for providing an injection of a rinsing medium from said nozzle toward the interior of said channel.

8. A liquid sample analyzer according to claim 7 in which said rinsing medium is one of the group consisting of air, distilled water or buffer solution.

* * * * *